United States Patent [19]

Itoh et al.

[11] Patent Number: 4,584,391

[45] Date of Patent: Apr. 22, 1986

[54] METHOD FOR THE PREPARATION OF ISOSORBIDE-5-NITRATE AND SODIUM ISOSORBIDE-5-NITRATE HYDRATE AS A PRECURSOR THEREOF

[75] Inventors: Toshio Itoh, Urawa; Susumu Ishiguro, Omiya; Fumitake Shimada, Kasukabe; Kenichi Ishibashi, Urawa, all of Japan

[73] Assignee: Toshin Chemical Co. Ltd., Tokyo, Japan

[21] Appl. No.: 674,144

[22] Filed: Nov. 23, 1984

[30] Foreign Application Priority Data

Nov. 25, 1983 [JP] Japan .................... 58-221476
Nov. 25, 1983 [JP] Japan .................... 58-221477

[51] Int. Cl.$^4$ ............................ C07D 493/04
[52] U.S. Cl. .................................... 549/464
[58] Field of Search ............................ 549/464

[56] References Cited

U.S. PATENT DOCUMENTS 3,886,186  5/1975  Dvonch et al. .................... 549/464

OTHER PUBLICATIONS

Hayward et al., Canadian J. of Chem., vol. 45, pp. 2191-2194 (1967).

Primary Examiner—Henry R. Jiles
Assistant Examiner—Bernard I. Dentz
Attorney, Agent, or Firm—Brisebois & Kruger

[57] ABSTRACT

A novel and efficient method is proposed for the preparation of isosorbide-5-nitrate which is a promising medicinal compound for several diseases due to disorder in heart. The method comprises direct nitration of isosorbide with a concentrated nitric acid in a specific reaction medium containing an aromatic hydrocarbon solvent, e.g. benzene, in addition to conventional acetic acid and acetic anhydride. After neutralization of the reaction mixture and removal of the dinitrate as a by-product therefrom, the reaction mixture is admixed with an aqueous solution of sodium hydroxide so that a sodium salt of isosorbide-5-nitrate is precipitated in the form of a hydrate, which is a novel compound not known in the prior art. This hydrate sodium salt is then decomposed with an acid to give the desired isosorbide-5-nitrate in a high yield.

8 Claims, 2 Drawing Figures

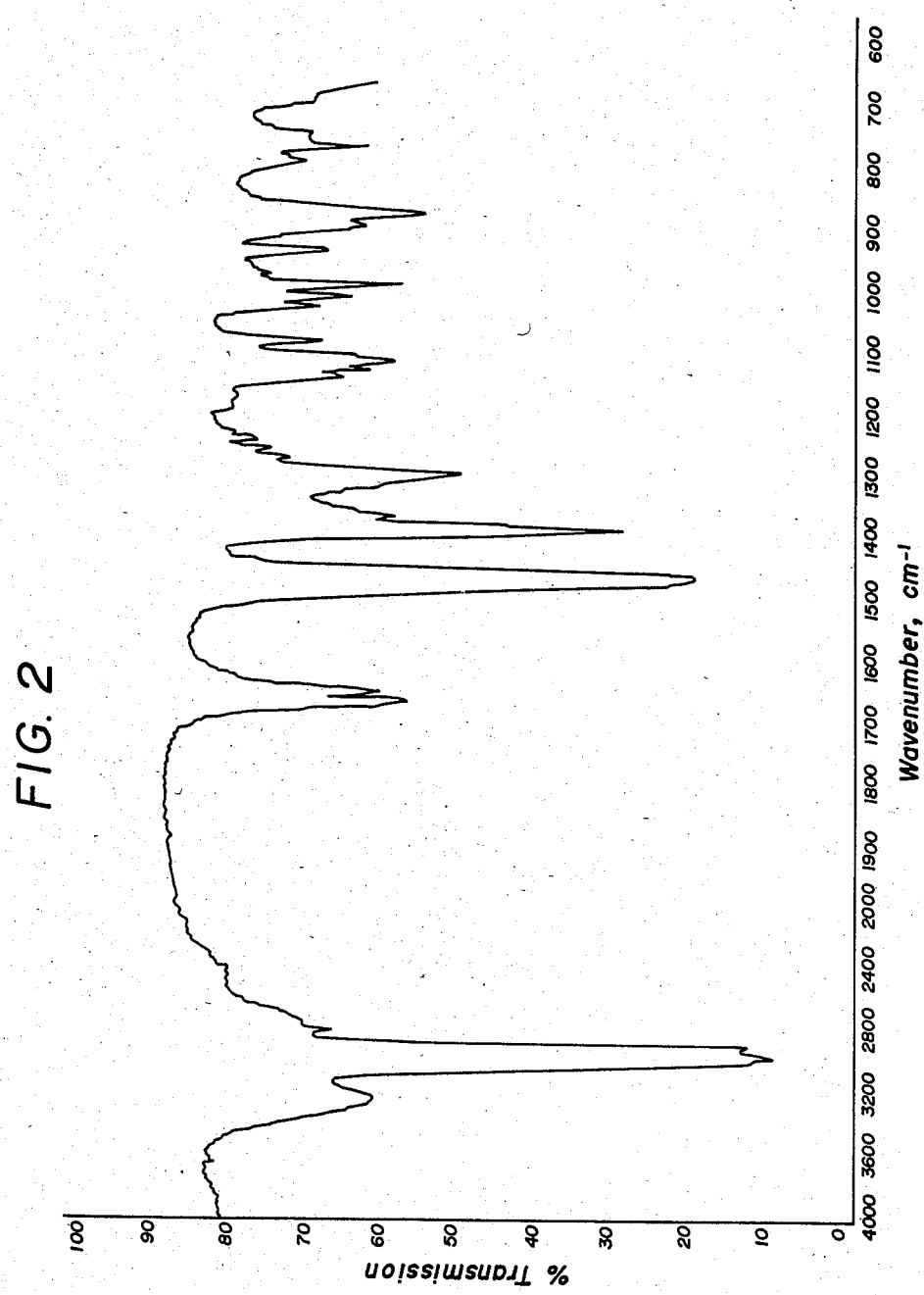

METHOD FOR THE PREPARATION OF ISOSORBIDE-5-NITRATE AND SODIUM ISOSORBIDE-5-NITRATE HYDRATE AS A PRECURSOR THEREOF

BACKGROUND OF THE INVENTION

The present invention relates to a method for the preparation of a useful medicine isosorbide-5-nitrate and sodium isosorbide-5-nitrate hydrate, which is a novel compound not known or not described in the literatures, as a precursor in the preparation thereof.

Isosorbide-5-nitrate is a compound expressed by the formula

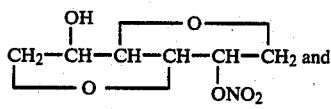

known for a long time as a metabolic product in a living body of the so-called isosorbide nitrate or isosorbide-2,5-dinitrate having a vasodilatating activity to peripheral veins. It has been recently discovered in the course of the investigations undertaken to elucidate the mechanism for the effectiveness of the latter compound that isosorbide-5-nitrate itself is useful and promising as a therapeutic medicine for several heart troubles due to disorder in coronary arteries such as angina pectoris, mycocardial infarction and the like.

Several methods are known for the preparation of isosorbide-5-nitrate which can be classified into 4 types as a rough classification including:

(1) a method of the nitration of isosorbide, i.e. 1,4:3,6-dianhydrosorbitol, with concentrated nitric acid or acetyl nitrate in a solvent mixture of acetic acid and acetic anhydride disclosed in Canadian Journal of Chemistry, volume 45, page 2191, DE-A No. 2,221,080, U.S. Pat. No. 3,886,186 and Japanese Patent Publication 55-29996;

(2) a method of partial hydrolysis of isosorbide-2,5-dinitrate obtained by the complete nitration of isosorbide disclosed in Organic Magnetic Resonance, volume 3, page 693, EU-A No. 59,664 and Japanese Patent Kokai No. 57-156492;

(3) a method starting from isomannide disclosed in West German Pat. No. 2,903,927, FR-A No. 2,447,933 and Japanese Patent Kokai No. 55-127393; and (4) a method in which the hydroxyl group at the 5-position of isosorbide is nitrated with the hydroxyl group at the 2-position selectively protected by a suitable protecting group followed by the elimination of the protecting group disclosed in DE-A No. 3,028,873, DE-A No. 3,128,102, EU-A No. 45,076, EU-A No. 57,847, EU-A No. 64,194 and Japanese Patent Kokai No. 57-144288, 57-185286, 58-18385 and 58-18386.

These prior art methods are, however, not quite satisfactory due to the problems and disadvantages in one or more respects. For example, the reaction mixture after the direct nitration of isosorbide according to the above described first method contains 4 compounds including isosorbide-2,5-dinitrate, isosorbide-2-nitrate, isosorbide-5-nitrate as the desired reaction product and the unreacted isosorbide while no efficient method is known for the separation of these components into respective pure forms. In particular, the explosiveness of the dinitrate excludes the possibility of undertaking heating or concentration under reduced pressure of the reaction mixture in the purification of the desired product so that the only possible technique applicable to the purification of the product in this case is the column chromatography. In addition, the reaction of nitration must be performed at a relatively low temperature by taking utmost care for the handling of the nitrating agent when it is explosive and dangerous acetyl nitrate greatly decreasing the productivity of the process. These problems and disadvantages, along with the low yield of about 20% of the desired product based on the theoretical value, hardly afford the practicability of the method of direct nitration.

The second method of the partial hydrolysis of isosorbide-2,5-dinitrate is also quite disadvantageous from the standpoint of practicability because no hydrolyzing agent satisfactory both in the activity and in the selectivity is known. For example, the activity of hydrochloric acid as a hydrolyzing agent is low so that the reaction of hydrolysis can be completed only by taking an unduly long time. The hydrolysis reaction of the dinitrate by use of a hydrazine derivative suffers from the large amount of isosorbide-2-nitrate formed as a byproduct so that the reaction mixture after completion of the hydrolysis reaction must be purified by the techniques of column chromatography in order to isolate the desired product.

The third method from isomannide as the starting material has a problem of the low availability of isomannide in comparison with isosorbide. In addition, the intermediate with tosylation of the hydroxyl group at the 2-position must be further converted into a benzoate. The nitration of the hydroxyl group at the 5-position can proceed only by use of the explosive and dangerous acetyl nitrate. It is of course that the benzoate group at the 2-position must be finally eliminated. Therefore, the practical and industrial value of this method is greatly decreased when the complicated and long sequence of the steps is taken into consideration.

The last of the above described prior art methods is also disadvantageous from the standpoint of industrialization due to the long and complicated sequence of steps including the protection of the hydroxyl group at the 2-position with a protecting group followed by the elimination thereof after the nitration of the hydroxyl group at the 5-position. In addition, the low selectivity of the reaction in this method limits the practical applicability of the method to the industrial production because the reaction mixture contains large amounts of byproducts which can be separated from the desired product only by the column chromatographic techniques if not to mention the relatively low yield of the desired product.

SUMMARY OF THE INVENTION

It is therefore an object of the present invention to provide a novel and improved method for the preparation of isosorbide-5-nitrate free from the above described problems and disadvantages in the prior art methods. The remarkable improvements obtained in the inventive method over the conventional methods are achieved primarily by the proper selection of the solvent or solvents used in the nitration of the starting isosorbide, by virtue of which the amounts of undesirable byproducts such as isosorbide-2,5-dinitrate can be greatly decreased. In addition, reaction of the reaction mixture after removal of the byproducts with an aqueous solution of sodium hydroxide gives sodium isosorbide-5-nitrate hydrate, which is a novel compound not known nor described in any prior art literatures, in a highpurity crystalline form from which the desired isosorbide-5-nitrate can readily be obtained in a very high purity.

The method of the present invention for the preparation of isosorbide-5-nitrate comprises the steps of:

(a) nitrating isosorbide with concentrated nitric acid in a reaction medium comprising an aromatic hydrocarbon solvent;

(b) neutralizing the reaction mixture after completion of the nitration reaction in the step (a);

(c) removing isosorbide-2,5-dinitrate as a byproduct of the nitration reaction from the thus neutralized reaction mixture;

(d) reacting the reaction mixture freed from isosorbide-2,5-dinitrate with an aqueous solution of sodium hydroxide to form a sodium isosorbide-5-nitrate hydrate of the formula $$[C_6H_9NO_6Na]^+[OH]^-\cdot nH_2O,$$

in which n is a positive number of 2 to 8; and (e) treating the sodium isosorbide-5-nitrate hydrate with an acid in a solvent to neutrality.

DETAILED DESCRIPTION OF THE PREFERRED EMBODIMENTS

Figure 1:
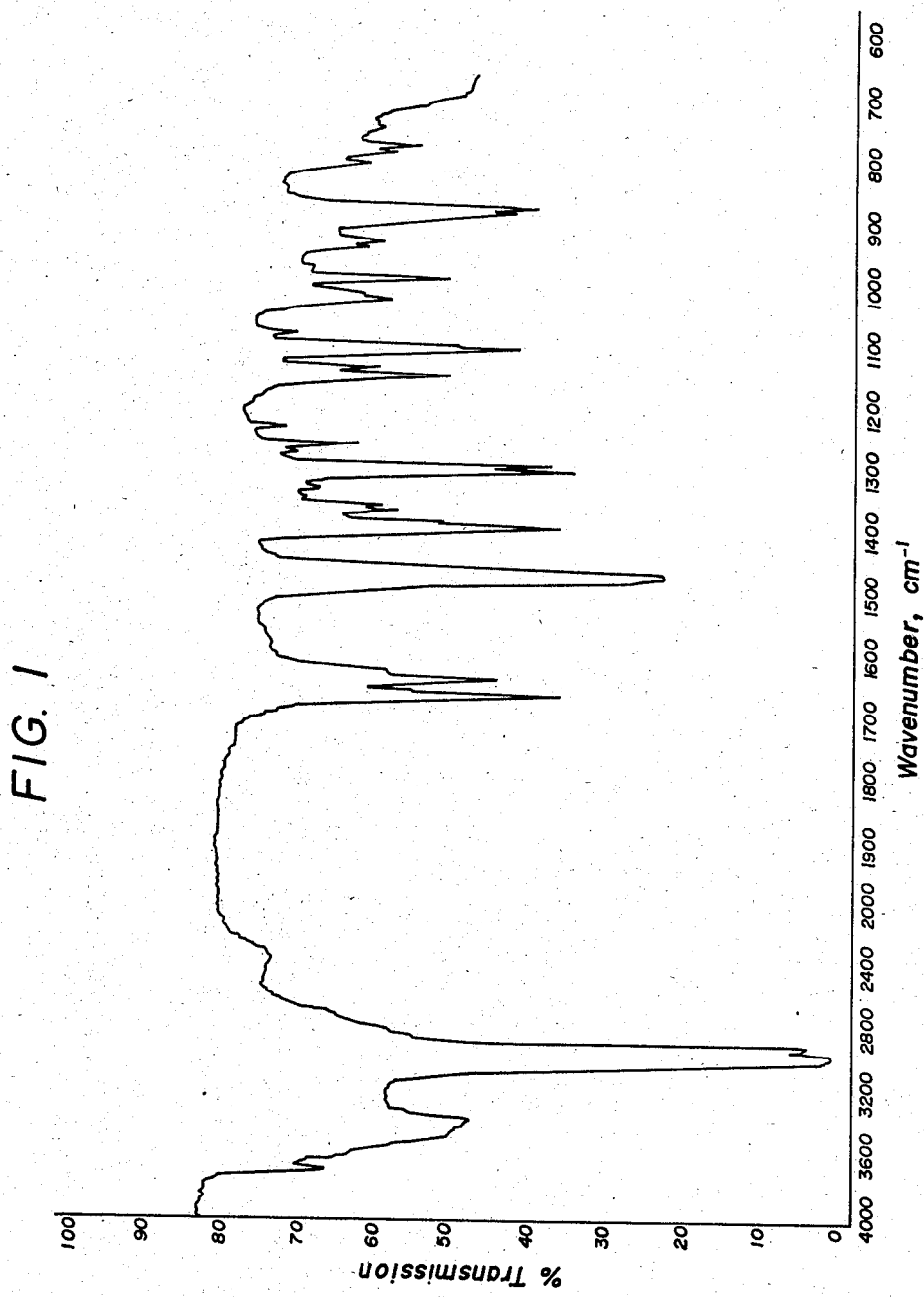

The first step of the inventive method is the nitration of isosorbide with concentrated nitric acid in a reaction medium comprising an aromatic hydrocarbon solvent. The aromatic hydrocarbon solvent usable in this case is exemplified by benzene, toluene, xylene, cumene, tetrahydronaphthalene and the like aromatic hydrocarbons and they can be used either singly or as a combination of two kinds or more according to need. A preferable aromatic hydrocarbon solvent is benzene. It is preferable that the aromatic hydrocarbon solvent is used as a mixture with a non-aromatic solvent which may be a lower alkanoic acid such as acetic acid or an acid anhydride corresponding to the lower alkanoic acid such as acetic anhydride. The volume fraction of the aromatic hydrocarbon solvent should preferably be in the range from 40 to 85%. Thus, one of the most preferable reaction media is a mixture of benzene, acetic acid and acetic anhydride in a proportion of 40 to 70%, 15 to 30% and 15 to 30% by volume, respectively. The concentration of the isosorbide in the reaction mixture is preferably in the range from 10 to 25% by weight based on the solvent or solvent mixture.

The nitrating agent used in the nitration of isosorbide in the step (a) of the inventive method is a concentrated nitric acid which is preferably a fuming nitric acid. The concentrated nitric acid is used in an amount of 1.0 to 1.5 moles or, preferably, 1.1 to 1.3 moles as $HNO_3$ per mole of the isosorbide as the starting material in the reaction mixture.

A preferable procedure for performing the nitration reaction of isosorbide is, for example, that isosorbide is added to the solvent or solvent mixture to be completely dissolved therein with heating and the fuming nitric acid is directly added dropwise to the reaction mixture kept at a temperature in the range of 10° to 60° C. or, preferably, 30° to 40° C. under agitation and, after completion of the dropwise addition of the fuming nitric acid, the reaction mixture is further agitated for additional 2 hours at room temperature.

The second step of the inventive method is the neutralization of the thus obtained reaction mixture. This is performed by pouring the reaction mixture into a sufficient volume of ice water and the diluted aqueous solution is neutralized by adding an alkali hydroxide or alkali carbonate which may be in a solid form or in the form of an aqueous solution of a relatively high concentration so that the aqueous layer may have a value of pH of 6.8 to 7.0.

The third step of the inventive method is the separation of the isosorbide-2,5-dinitrate from the thus neutralized reaction mixture which can be readily performed since the reaction mixture after the dilution with ice water and neutralization with an alkali in the foregoing step is separated into two phases of an organic layer and an aqueous layer while the dinitrate as the byproduct and the desired isosorbide-5-nitrate are contained in the former and latter layers, respectively. Therefore, conventional methods for the phase separation of immiscible liquids can afford a means for the separation of the dinitrate from the desired product. It is preferable that, in order to obtain a yield of the desired product as high as possible, the organic solution obtained in the above phase separation is further extracted with water repeatedly and the aqueous extracts are altogether combined with the aqueous solution obtained in the phase separation.

The aqueous solution thus obtained contains the desired product of isosorbide-5-nitrate as the principal ingredient which should preferably be extracted by use of a non-aromatic solvent substantially immiscible or not freely miscible with water and inert to the product. Suitable solvents for the extraction purpose include chloroform, methylene chloride, methylchloroform, ethyl acetate, butyl acetate, methyl ethyl ketone, methyl isobutyl ketone and the like, among which methyl ethyl ketone is the most preferable in respect of the efficiency of extraction. The methyl ethyl ketone extract is then evaporated under reduced pressure to remove the solvent so that an oily residue mainly composed of the isosorbide-5-nitrate is left.

The next-coming step is the reaction of the isosorbide-5-nitrate with sodium hydroxide. This reaction is performed by dissolving the above obtained oily matter in water or a suitable organic solvent such as isopropyl alcohol and admixing the solution with an aqueous solution of sodium hydroxide in a relatively high concentration of, for example, 30% by weight whereupon a white crystalline material precipitates immediately. This crystalline material is already in a considerably high purity but can be purified, if desired, by the technique of reprecipitation utilizing the solubility behavior thereof that it is hardly soluble in isopropyl alcohol, acetone and chloroform but soluble in methyl and ethyl alcohols. For example, the white crystalline material is dissolved in a small volume of ethyl alcohol and chloroform is added to the ethyl alcohol solution so that the product can be obtained in a still higher purity.

The thus obtained product is in the form of white flaky or scaly crystals melting at 101° to 102° C. and the results of the chemical and physical analyses undertaken with this white crystalline product, including infrared absorption spectroscopy, measurement of optical rotation, determination of water content and elementary analysis, indicate that it is sodium isosorbide-5-nitrate hydrate expressed by the formula $$[C_6H_9NO_6Na]^+[OH]^-\cdot nH_2O,$$

in which n is a positive number of 2 to 8. This compound is a novel compound not described in any prior art literatures.

This product is unstable in atmospheric air even at room temperature and gradually loses the water content and absorbs carbon dioxide with decreasing luster when kept standing in an ambient atmosphere. It is soluble in water in an amount of 20 to 25% by weight and the aqueous solution exhibits a value of pH of about 12.0. It is readily decomposed in an aqueous solution or in a methyl alcohol solution but stable in a concentrated aqueous solution of sodium hydroxide having a higher value of pH than above. The water content or the value of n in the above given formula of this product is about 8 moles of $H_2O$ per mole before purification by the reprecipitation but it appears that the compound is relatively stable when the value of n is in the range from 2 to 4.

It is noteworthy that the formation of the crystalline hydrated alkali metal salt is specific to sodium hydroxide as the alkali source to be added to the oily matter mainly composed of isosorbide-5-nitrate and replacement of sodium hydroxide with potassium hydroxide, ammonia or an alkali carbonate in the form of an aqueous solution never gives a corresponding hydrated alkali or ammonium salt of isosorbide-5-nitrate in a crystalline form.

The final step for the preparation of isosorbide-5-nitrate is the decomposition of the above obtained hydrated sodium salt thereof with an acid. This reaction of decomposition can readily take place when the hydrated sodium salt is dissolved or dispersed in a suitable solvent and an acid is added thereto in an amount sufficient to ensure neutrality of the mixture so that the sodium salt is decomposed to isolate free isosorbide-5-nitrate. The solvents usable for this purpose include water, organic solvents and mixtures thereof, the organic solvent being selected preferably from the group consisting of chloroform, methylene chloride, methylchloroform, ethyl acetate, butyl acetate, methyl ethyl ketone and methyl isobutyl ketone of which methyl ethyl ketone is more preferable. In particular, best results can be obtained by use of a mixture of methyl ethyl ketone and water although water alone may serve as the solvent. That is, the hydrated sodium salt of isosorbide-5-nitrate is dissolved in a mixture of methyl ethyl ketone and water and decomposed by adding an acid in such an amount that the value of pH of the mixture is about 7.0. The acid used here may be an inorganic acid such as hydrochloric and sulfuric acids or an organic acid such as acetic and methanesulfonic acids. The thus neutralized mixture is then subjected to phase separation into aqueous and organic layers and the organic solvent in the organic solution is removed by evaporation under reduced pressure so that the desired isosorbide-5-nitrate is obtained in a crude crystalline form.

The crude crystalline isosorbide-5-nitrate can be efficiently purified, if desired, in a good yield by the techniques of recrystallization using chloroform, methylene chloride, or a mixture of n-hexane and methyl or ethyl alcohol as the solvent. The physicochemical parameters of the thus purified specimen of isosorbide-5-nitrate are identical with those of the authentic sample of the compound including the infrared absorption spectrum, optical rotation, melting point and behavior in the thinlayer chromatography.

To give a summary, as is understood from the above description, the inventive method has several advantageous features that the efficiency of the nitration reaction of isosorbide to form isosorbide-5-nitrate is greatly improved by using an aromatic hydrocarbon solvent or, in particular, benzene as a component of the reaction medium, that the nitration reaction can be undertaken with safety because the reaction is performed without using explosive and dangerous acetyl nitrate, that the novel compound sodium isosorbide-5-nitrate hydrate can be obtained in a very high purity by a simple treatment of the nitration product and that the hydrated sodium salt can readily be converted into the final product of isosorbide-5-nitrate in a highly pure crystalline form. Therefore, the present invention provides a very promising method for the industrial production of isosorbide-5-nitrate as a useful medicine.

In the following, the method of the present invention and characterization of the novel compound sodium isosorbide-5-nitrate hydrate are described in more detail by way of examples.

EXAMPLE 1

Into a solvent mixture composed of 450 ml of benzene, 150 ml of acetic acid and 150 ml of acetic anhydride were added and dissolved 150 g of isosorbide under agitation with heating at 50° to 55° C. to form a reaction mixture. After cooling to about 30° C., 82.5 g of fuming nitric acid having a specific gravity of 1.50 and a purity of 94% were added dropwise to the reaction mixture kept at 30° to 35° C. over a period of 2 hours followed by further continued agitation at room temperature for additional 2 hours from the end of the dropwise addition of the whole volume of the fuming nitric acid.

The reaction mixture was then poured into 1 liter of ice water and the value of pH of the mixture was brought to 7.0 by carefully adding a 30% by weight aqueous solution of sodium hydroxide under agitation. The reaction mixture separated into two layers of organic and aqueous layers by standing was subjected to phase separation and the organic solution was extracted three times each with 150 ml of water. The aqueous extracts were combined with the aqueous solution obtained in the first phase separation and the thus combined aqueous solution was extracted four times each with 500 ml of methyl ethyl ketone. Distillation of this methyl ethyl ketone extract under reduced pressure left 150 g of an oily matter.

The oily matter was dissolved in 500 ml of isopropyl alcohol and the solution chilled at 0° C. was admixed gradually with 100 ml of a 30% by weight aqueous solution of sodium hydroxide so that a white crystalline material immediately precipitated. After agitation for additional 2 hours at 0° C., the mixture was filtered to collect the crystalline material which was then washed with a small volume of isopropyl alcohol and air-dried overnight at room temperature to give 148 g of a crystalline product. This product was subsequently identified to be crude crystals of sodium isosorbide-5-nitrate hydrate and the above mentioned yield was about 47.6% of the theoretical value assuming a water content of 4 moles per mole of the nitrate.

The above obtained crude crystals of sodium isosorbide-5-nitrate hydrate were purified by reprecipitation. Thus, 22 g of the crude crystals were dissolved in 80 ml of ethyl alcohol and 200 ml of chloroform were added to the ethyl alcohol solution after filtration to remove a small amount of insoluble matter so that precipitation of white crystals immediately took place. The crystals were collected by filtration and washed with 30 ml of chloroform followed by drying at 40° C. for 2 hours in a stream of nitrogen to give 16.4 g of white lustrous crystals in a flaky or scaly form. The yield in this purification process was 74.5%.

The physicochemical parameters of this crystalline product were as follows: melting point 101° to 102.5° C.; content of water 23.4% by the Karl Fischer's method; content of sodium 7.7% by the acid titration; characteristic absorption bands by the nitro ester groups in the infrared absorption spectrum obtained by the paste method at 1621, 1288 and 1279 cm$^{-1}$ assigned to $NO_2$ and at 860 cm$^{-1}$ assigned to NO; and optical rotation $[\alpha]_D^{20}+106.4°$ (C 1.0; ethyl alcohol). The results of the elementary analysis for carbon, hydrogen and nitrogen were as given below together with the calculated values assuming the formula of $[C_6H_9NO_6Na].2.5H_2O$.

|  | C | H | N |
| --- | --- | --- | --- |
| Calculated, % | 26.09 | 5.47 | 5.10 |
| Found, % | 25.98 | 5.18 | 5.08 |

The infrared absorption spectrum of this purified product of sodium isosorbide-5-nitrate hydrate is shown in FIG. 1 of the accompanying drawing.

For comparison, a trial was made to obtain the same hydrated sodium salt starting from an authentic sample of isosorbide-5-nitrate. Thus, 20 g of pure crystals of isosorbide-5-nitrate were dissolved in 80 ml of water and the aqueous solution was admixed at 0° C. with 160 ml of a 30% by weight aqueous solution of sodium hydroxide so that precipitation of white crystals immediately took place. After agitation for additional 2 hours at 5° C. or below, the reaction mixture was filtered to collect the crystalline product which was dried overnight in a desiccator over sodium hydroxide. The yield of the thus obtained white flaky or scaly crystalline product was 28.4 g corresponding to 89.6% of the calculated value assuming a water content of 4 moles per mole of the sodium salt. Purification of this hydrated sodium salt by reprecipitation from an ethyl alcohol solution with chloroform as the precipitant gave 23.3 g of a purified product. The yield in this purification process was 82.0% and the overall yield from the starting isosorbide-5-nitrate was 73.5% assuming a water content of 4 moles per mole of the sodium salt. The physicochemical parameters of this purified product were: melting point 101° to 102° C.; content of water 23.4% by the Karl Fischer's method; content of sodium 7.7% by the acid titration; and optical rotation $[\alpha]_D^{20}+106.5°$ (C 1.0; ethyl alcohol). The infrared absorption spectrum of this product was identical with that of the purified product prepared by starting with the nitration of isosorbide.

EXAMPLE 2

A 84 g portion of the crude crystalline product of sodium isosorbide-5-nitrate hydrate prepared in Example 1 was suspended in a mixture of 148 ml of ice water and 296 ml of methyl ethyl ketone and the pH of the mixture was adjusted to 7.0 by adding a cold hydrochloric acid of 6-normal concentration. The mixture separated into the aqueous and organic layers by standing was subjected to phase separation and the aqueous solution was extracted three times each with 148 ml of methyl ethyl ketone to combine the extracts with the organic solution obtained in the first phase separation. After drying with anhydrous magnesium sulfate, the methyl ethyl ketone solution was distilled under reduced pressure to remove the solvent leaving 45 g of crude crystals of isosorbide-5-nitrate. This crude crystalline product of isosorbide-5-nitrate was purified by recrystallization using 180 ml of chloroform to give 40 g of a white crystalline product of pure isosorbide-5-nitrate.

The physicochemical parameters of this purified product of isosorbide-5-nitrate, which gave a single spot in the thin-layer chromatography by use of a 10:1 by volume mixture of chloroform and methyl alcohol as the developer, were: melting point 90.6° C.; optical rotation $[\alpha]_D^{20}+175.6°$ (C 1.0; ethyl alcohol); and the characteristic bands in the infrared absorption spectrum by the nitro ester groups at 1650, 1635 and 1281 cm$^{-1}$ assigned to $NO_2$ and at 846 cm$^{-1}$ assigned to NO. The infrared absorption spectrum of this purified isosorbide-5-nitrate shown in FIG. 2 is almost identical with that of the authentic sample of the compound.

EXAMPLE 3

Into a reaction mixture at 35° C. prepared by completely dissolving 1.5 kg of isosorbide in a solvent mixture composed of 4.5 liters of benzene, 1.5 liters of acetic acid and 1.5 liters of acetic anhydride with agitation for 20 minutes at 55° C. was added dropwise 0.825 kg of a fuming nitric acid having a specific gravity of 1.50 and a purity of 94% over a period of 2 hours while the temperature of the reaction mixture was kept at 30° to 35° C. followed by further agitation of the mixture for additional two hours at room temperature. The reaction mixture was poured into 10 liters of ice water and neutralized by adding 3.35 kg of anhydrous sodium carbonate so that the pH of the mixture was about 6.8 to 7.0. The mixture separated into the aqueous and organic layers by standing was subjected to phase separation and the organic solution was extracted three times each with 1.5 liters of water.

The thus obtained aqueous extracts were combined together with the aqueous solution obtained in the first phase separation and the combined aqueous solution was extracted 4 times each with 6 liters of methyl ethyl ketone. The methyl ethyl ketone extracts as combined were then subjected to distillation under reduced pressure to remove the solvent leaving 1.527 kg of an oily matter, which was dissolved in 2 liters of water. The aqueous solution was chilled at 0° C. and 2 liters of a 30% by weight aqueous solution of sodium hydroxide were gradually added thereto under agitation so that white crystals precipitated immediately.

The precipitated white crystals of sodium isosorbide-5-nitrate hydrate were collected by filtration and washed with a small volume of the aqueous solution of sodium hydroxide. The crystals of the hydrated sodium salt was then suspended in a solvent mixture of 2 liters of ice water and 3 liters of methyl ethyl ketone and the pH of the suspension was brought to 6.8 to 7.0 by the addition of a chilled 6-normal hydrochloric acid. The mixture was separated into aqueous and organic layers by standing and subjected to phase separation. The aqueous solution obtained by the phase separation was extracted 3 times each with 2 liters of methyl ethyl ketone and the methyl ethyl ketone extracts were combined with the organic solution obtained in the first phase separation. The thus combined organic solution was, after dehydration with anhydrous magnesium sulfate, distilled under reduced pressure to remove the solvent leaving 1.112 kg of a solid product. This crude product was purified by recrystallization using 4.0 liters of chloroform to give 0.890 kg of a purified product which was identified to be isosorbide-5-nitrate giving a single spot in the thin-layer chromatography by use of a 10:1 by volume solvent mixture of chloroform and methyl alcohol as the developer. The yield of this purified product was 45.4% of the theoretical value. The physicochemical parameters of this purified isosorbide-5-nitrate were: melting point 91° C. and optical rotation $[\alpha]_D^{20} + 175.8°$.

EXAMPLE 4

Into a solvent mixture composed of 60 ml of benzene and 15 ml of acetic anhydride were added and dissolved 15 g of isosorbide with heating. Thereafter, the mixture was cooled to 35° C. and 7.5 g of a fuming nitric acid having a specific gravity of 1.50 and a purity of 94% were added dropwise into the mixture over a period of 1 hour while the temperature of the mixture was kept at 35° C. After completion of the dropwise addition of the fuming nitric acid, the reaction mixture was further agitated for additional 2 hours and then poured into 150 ml of ice water followed by the adjustment of the pH of the mixture to 6.8 to 7.0 by adding anhydrous sodium carbonate. The mixture, separated into an organic layer and an aqueous layer by standing, was subjected to phase separation and the organic solution was extracted 3 times each with 20 ml of water. The aqueous extracts were combined with the aqueous solution obtained in the first phase separation and the thus combined aqueous solution was extracted 4 times each with 50 ml of methyl ethyl ketone. The organic extract as combined was distilled under reduced pressure to remove the organic solvent leaving 13.0 g of an oily residue.

The above obtained oily residue was dissolved in 18 ml of water and this aqueous solution was admixed with 20 ml of a 30% by weight aqueous solution of sodium hydroxide under chilling with ice so that white crystals precipitated immediately. Agitation of the mixture at 0° C. for 2 hours was followed by filtration to collect the crystalline product which was then washed with a small volume of the same aqueous solution of sodium hydroxide. The crystalline product was then suspended in a mixture of 15 ml of ice water and 20 ml of methyl ethyl ketone and the pH of the mixture was brought to 6.8 to 7.0 by adding a 6-normal hydrochloric acid under agitation. The aqueous layer separated on standing of the mixture was taken by phase separation and extracted 3 times each with 20 ml of methyl ethyl ketone and the extracts were combined together. After dehydration with anhydrous magnesium sulfate, the combined methyl ethyl ketone extract was distilled under reduced pressure to remove the solvent leaving 8.0 g of a solid residue which was dissolved in chloroform and re-precipitated with addition of n-hexane to give 5.8 g of a white crystalline product identified to be purified isosorbide-5-nitrate. The above mentioned yield of the product was 29.6% of the theoretical value.

EXAMPLES 5 TO 12

The procedure in each of these Examples was substantially the same as in Example 4 above except that the combination of the solvents to form the reaction medium was as indicated in the table below. In some of the Examples, the amount of the fuming nitric acid was also varied as shown in the table. The yield of the desired product isosorbide-5-nitrate in each of the Examples is shown in the same table.

TABLE

| Example No. | Fuming nitric acid taken, g | Fuming nitric acid moles/mole isosorbide | Benzene | Toluene | Xylene | Tetrahydronaphthalene | Cyclohexane | Acetic acid | Acetic anhydride | Yield of isosorbide-5-nitrate g | Yield of isosorbide-5-nitrate % of theoretical |
|---|---|---|---|---|---|---|---|---|---|---|---|
| 4 | 7.5 | 1.09 | 60 | — | — | — | — | — | 15 | 5.8 | 29.6 |
| 5 | 7.5 | 1.09 | — | 60 | — | — | — | — | 15 | 5.4 | 27.6 |
| 6 | 7.5 | 1.09 | — | — | 60 | — | — | — | 15 | 5.2 | 26.5 |
| 7 | 7.5 | 1.09 | — | — | — | 60 | — | — | 15 | 5.2 | 26.5 |
| 8 | 7.5 | 1.09 | — | — | — | — | 60 | — | 15 | 2.7 | 13.8 |
| 9 | 7.5 | 1.09 | — | — | — | — | — | 60 | 15 | 5.5 | 28.1 |
| 10 | 7.5 | 1.09 | 45 | — | — | — | — | 15 | 15 | 6.4 | 32.7 |
| 11 | 8.25 | 1.20 | 45 | — | — | — | — | 15 | 15 | 8.8 | 44.9 |
| 12 | 9.00 | 1.30 | 45 | — | — | — | — | 15 | 15 | 6.8 | 34.7 |

What is claimed is:

1. Sodium isosorbide-5-nitrate hydrate of the formula $[C_6H_9NO_6Na]^+[OH]^-.nH_2O$, in which n is a positive number in the range from 2 to 8.

2. A method for the preparation of sodium isosorbide-5-nitrate hydrate which comprises the successive steps of nitrating isosorbide with a concentrated nitric acid in a reaction medium comprising an aromatic hydrocarbon solvent, neutralizing the reaction mixture containing the nitration products of isosorbide, removing isosorbide-2,5-dinitrate from the reaction mixture and adding an aqueous solution of sodium hydroxide to the reaction mixture.

3. A method for the preparation of isosorbide-5-nitrate which comprises the successive steps of:
   (a) nitrating isosorbide with a concentrated nitric acid in a reaction medium which is a mixture comprising an aromatic hydrocarbon solvent;
   (b) neutralizing the reaction mixture containing the nitrates of isosorbide;
   (c) removing isosorbide-2,5-dinitrate from the reaction mixture;
   (d) adding an aqueous solution of sodium hydroxide to the reaction mixture to form sodium isosorbide-5-nitrate hydrate;
   (e) separating the sodium isosorbide-5-nitrate hydrate from the reaction mixture;
   (f) dispersing the sodium isosorbide-5-nitrate hydrate in a solvent medium; and
   (g) decomposing the sodium isosorbide-5-nitrate hydrate with an acid.

4. The method as claimed in claim 3 wherein the aromatic hydrocarbon solvent is benzene.

5. The method as claimed in claim 3 wherein the nitration reaction in the step (a) is carried out at a temperature in the range from 30° to 40° C.

6. The method as claimed in claim 3 wherein the concentrated nitric acid is a fuming nitric acid.

7. The method as claimed in claim 3 wherein the solvent medium used in the step (f) is a mixture of methyl ethyl ketone and water.

8. The method as claimed in claim 4 wherein the reaction medium in the step (a) is a mixture of benzene, acetic acid and acetic anhydride.

* * * * *